United States Patent
Lee et al.

(10) Patent No.: US 9,733,196 B2
(45) Date of Patent: Aug. 15, 2017

(54) UPPER SURFACE FOREIGN MATERIAL DETECTING DEVICE OF ULTRA-THIN TRANSPARENT SUBSTRATE

(71) Applicant: Nanoprotech Co., Ltd., Daejeon (KR)

(72) Inventors: Hyung Seok Lee, Seoul (KR); Yeong Ryeol Kim, Daejeon (KR); Cheul Ock Chae, Gunsan-si (KR); Jin Yong Kim, Daejeon (KR); Soung Jin Kim, Daejeon (KR)

(73) Assignee: Nanoprotech Co., Ltd., Daejeon (KR)

( * ) Notice: Subject to any disclaimer, the term of this patent is extended or adjusted under 35 U.S.C. 154(b) by 2 days.

(21) Appl. No.: 14/949,335

(22) Filed: Nov. 23, 2015

(65) Prior Publication Data

US 2016/0327494 A1    Nov. 10, 2016

(30) Foreign Application Priority Data

May 8, 2015    (KR) ........................ 10-2015-0064527

(51) Int. Cl.
| | |
|---|---|
| *G01N 21/00* | (2006.01) |
| *G01N 21/94* | (2006.01) |
| *G01N 21/958* | (2006.01) |
| *G01N 21/47* | (2006.01) |
| *G01N 21/95* | (2006.01) |
| *G01N 21/88* | (2006.01) |
| *G01N 21/896* | (2006.01) |

(52) U.S. Cl.
CPC .......... *G01N 21/94* (2013.01); *G01N 21/958* (2013.01); *G01N 21/9501* (2013.01); *G01N 2021/4735* (2013.01); *G01N 2021/8841* (2013.01); *G01N 2021/8848* (2013.01); *G01N 2021/8967* (2013.01)

(58) Field of Classification Search
CPC ... G01N 2021/4735; G01N 2021/8841; G01N 2021/8967; G01N 21/94; G01N 21/958
USPC .... 356/239.1, 237.2, 341, 237.3, 239.7, 364
See application file for complete search history.

(56) References Cited

U.S. PATENT DOCUMENTS 5,072,128 A * 12/1991 Hayano .................. G01N 21/94
                                              250/226
2011/0187849 A1    8/2011 Kim et al.

FOREIGN PATENT DOCUMENTS

| KR | 10-2007-0107773 A | 11/2007 |
|---|---|---|
| KR | 10-2011-0088706 A | 8/2011 |

* cited by examiner

*Primary Examiner* — Sunghee Y Gray
(74) *Attorney, Agent, or Firm* — The Webb Law Firm (57) ABSTRACT

Provided are a foreign material detecting device and method for detecting only a foreign material on a surface of a substrate except for a foreign material on a lower surface of the substrate in a manufacturing process of a transparent substrate passing light therethrough, such as a glass substrate used in a flat panel display (FPD) such as a liquid crystal display (LCD), an organic light emitting diode (OLED), a plasma display panel (PDP), etc., a sapphire wafer used in some of semiconductors, or the like, and in a pattern forming process in a manufacturing process of the FPD and the semiconductor using the transparent substrate. More particularly, provided are a foreign material detecting device and method for detecting only a foreign material on a surface of an ultra-thin transparent substrate having a thickness of 0.3 T or less.

4 Claims, 7 Drawing Sheets

FIG. 1

PRIOR ART

FIG. 2

PRIOR ART

UPPER SURFACE FOREIGN MATERIAL DETECTING DEVICE OF ULTRA-THIN TRANSPARENT SUBSTRATE

CROSS-REFERENCE TO RELATED APPLICATION

This application claims priority to Korean Patent Application No. 10-2015-0064527 filed May 8, 2015, the disclosure of which is hereby incorporated in its entirety by reference.

TECHNICAL FIELD

The following disclosure relates to a foreign material detecting device and method for detecting only a foreign material on a surface of a substrate except for a foreign material on a lower surface of the substrate in a manufacturing process of a transparent substrate passing light therethrough, such as a glass substrate used in a flat panel display (FPD) such as a liquid crystal display (LCD), an organic light emitting diode (OLED), a plasma display panel (PDP), etc., a sapphire wafer used in some of semiconductors, or the like, and in a pattern forming process in a manufacturing process of the FPD and the semiconductor using the transparent substrate.

More particularly, the following disclosure relates to a foreign material detecting device and method for detecting only a foreign material on a surface of an ultra-thin transparent substrate having a thickness of 0.3 T or less.

BACKGROUND

Foreign materials may be generated due to several reasons in a manufacturing process of a transparent substrate having a thin thickness, a packaging process, a pattern forming process using the transparent substrate, and the like. In the case in which the foreign materials generated in these process environments are attached onto an upper surface of the substrate, they hinder fine patterns for pixels from being formed on the upper surface in the subsequent process to allow circuit patterns for forming the pixels not to be formed at corresponding positions, thereby causing defective pixels and decreasing a process yield. Therefore, a process of inspecting the foreign materials on the upper surface of the substrate should be performed during or after the manufacturing process.

A lower surface of the substrate contacts a transporting means in order to transport the substrate in a manufacturing process of a flat panel display (FPD) and a semiconductor. Therefore, much more foreign materials may be attached onto the lower surface of the substrate than onto the upper surface of the substrate. Since fine foreign materials having sizes smaller than those of pixels among the foreign materials on the lower surface of the substrate do not have an influence on characteristics of the pixels, the fine foreign materials on the lower surface of the substrate are permitted. Therefore, only the foreign materials on the upper surface of the substrate have been strictly inspected in the manufacturing process of the transparent substrate and the manufacturing process of the FPD and the semiconductor using the transparent substrate.

In the manufacturing process of the FPD and the semiconductor, in order to inspect the foreign materials, a vision inspection method using an image obtained by irradiating light and imaging reflected light by a camera among non-contact inspection methods that do not damage the surface of the substrate has been mainly used. In the case of using the transparent substrate, the light arrives at the lower surface of the transparent substrate, such that reflected light on the foreign materials on the lower surface is also transferred. Therefore, the foreign materials on the lower surface are imaged, thereby making it possible to make an excessive badness decision and have an influence on a manufacturing yield. Therefore, a method of inspecting only the foreign material on the upper surface without being affected by the foreign materials on the lower surface has been required.

Figure 1:
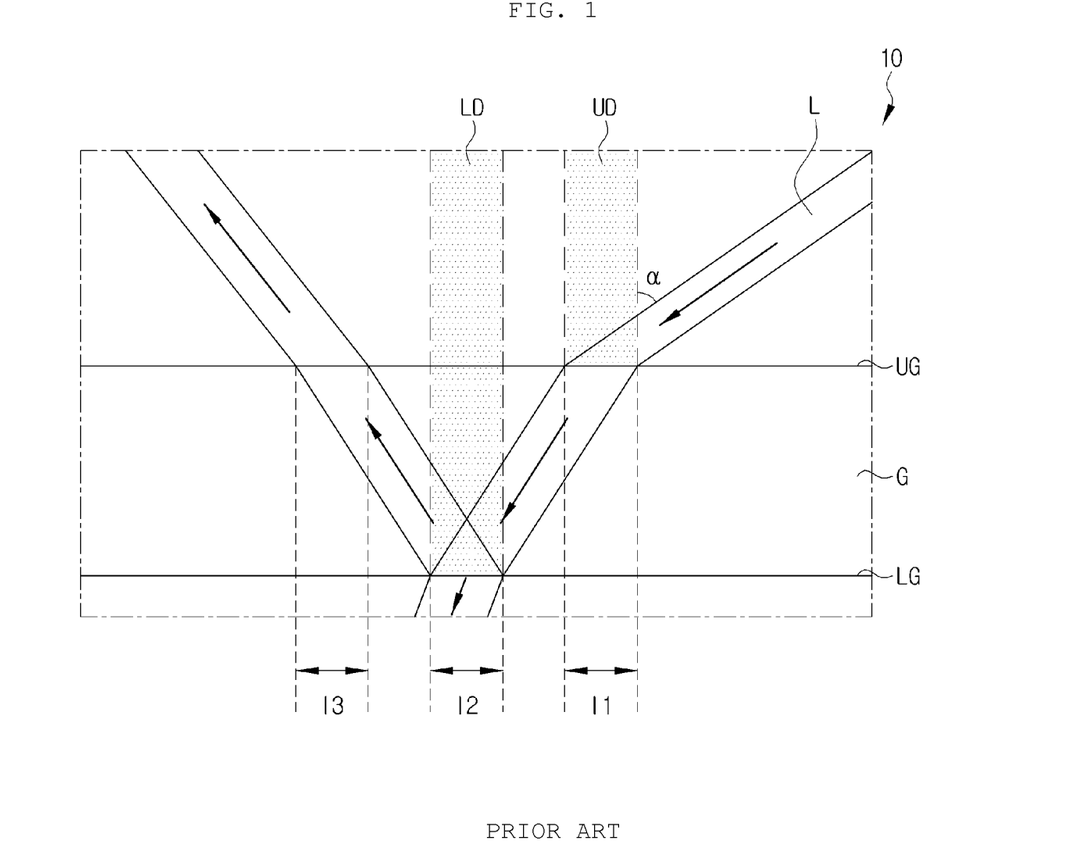
FIG. 1 is a conceptual diagram of a foreign material detecting device according to the related art.

In FIG. 1, a schematic view of a foreign material detecting device 10 of a transparent substrate having a thickness exceeding 0.3 T according to the related art is illustrated. Existing methods for detecting a foreign material on an upper surface UG of a transparent substrate G will be described with reference to FIG. 1. An upper surface foreign material and a lower surface foreign material of the transparent substrate G are distinguished from each other through an upper surface detecting part UD irradiating light L at an inclined angle θ so as to irradiate the light to both of the upper surface UG and a lower surface LG of the transparent substrate G, thereby inspecting scattered light of a first irradiation surface I1 irradiated to the upper surface UG of the transparent substrate G and a lower surface detecting part LD inspecting scattered light of a second irradiation surface I2 passing through the first irradiation surface I1 of the transparent substrate G, refracted, and then irradiated to the lower surface LG.

As illustrated in FIG. 1, in the case in which a thickness of the transparent substrate G exceeds 0.3 T, a section overlapped in a direction perpendicular to the transparent substrate G is not generated between the first irradiation surface I1 and the second irradiation surface I2, and is not also generated particularly between a third irradiation surface I3 on which light reflected on the lower surface LG is irradiated to the upper surface UG of the transparent substrate G and the second irradiation surface I2, such that the upper surface foreign material and the lower surface foreign material may be clearly distinguished from each other through the upper surface detecting part UD and the lower surface detecting part LD.

However, in the foreign material detecting device according to the related art as described above, in the case in which the transparent substrate is formed of an ultra-thin plate having a thickness of 0.3 T or less, the following problems occur.

Figure 2:
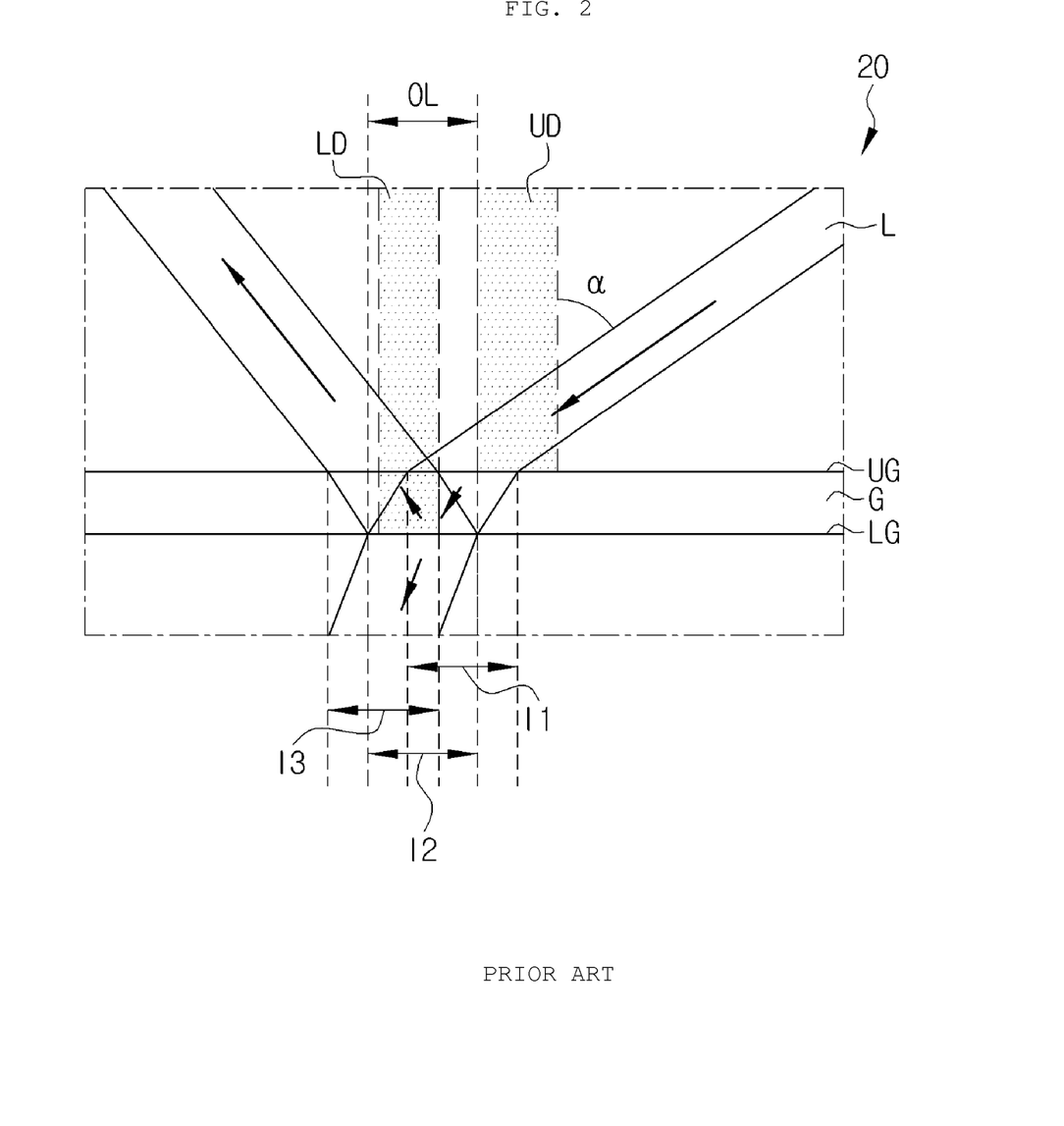
FIG. 2 is a conceptual diagram of a foreign material detecting device according to the related art applied to an ultra-thin transparent substrate.

In FIG. 2, a schematic view of a foreign material detecting device 20 of a transparent substrate having a thickness of 0.3 T or less according to the related art is illustrated.

As illustrated in FIG. 2, in the case in which the transparent substrate G is formed of an ultra-thin transparent plate, an overlapped portion OL is generated between the first irradiation surface I1 on which the light is irradiated to the upper surface UG of the transparent substrate G, the second irradiation surface I2 on which the light passing through the first irradiation surface I1 of the transparent substrate G and then refracted is irradiated to the lower surface LG, and between the second irradiation surface I1 and the third irradiation surface I3 on which the light reflected on the second irradiation surface I2 is irradiated to the upper surface UG. Particularly, since the overlapped portion OL covers the entire second irradiation surface I2, in the case of inspecting the second irradiation surface I2 by the lower surface detecting part LD, the second irradiation surface I2 is overlapped with the first and third irradiation surfaces I1 and I3, such that it is impossible to distinguish whether a foreign material is a foreign material present on the upper surface UG of the transparent substrate or a foreign material present on the lower surface LG of the transparent substrate.

Therefore, the development of a device for detecting only the foreign material on the upper surface of the transparent substrate having a thickness of 0.3 T or less has been demanded.

SUMMARY

An embodiment of the present invention is directed to providing an upper surface foreign material detecting device of an ultra-thin transparent substrate in which light reflected on a lower surface of the transparent substrate is removed to minimize an overlapped portion between an upper irradiation surface and a lower irradiation surface of the light, thereby minimizing a region in which it is impossible to distinguish an upper foreign material and a lower foreign material of the transparent substrate from each other.

Particularly, an embodiment of the present invention is directed to providing an upper surface foreign material detecting device of an ultra-thin transparent substrate in which light reflected on a lower surface of the transparent substrate is removed using transmittance characteristics of polarized light.

In one general aspect, an upper surface foreign material detecting device of an ultra-thin transparent substrate includes: a light source part irradiating light to a transparent substrate and irradiating light so as to be inclined at a Brewster angle corresponding to a material of the transparent substrate; a first detecting part detecting scattered light of a foreign material attached to an upper surface of the transparent substrate by the irradiated light; a second detecting part detecting scattered light of a foreign material attached to a lower surface of the transparent substrate by the irradiated light; and a control part comparing brightness of the scattered light detected through the first detecting part and brightness of the scattered light detected through the second detecting part to distinguish the foreign material attached to the upper surface of the transparent substrate and the foreign material attached to the lower surface of the transparent substrate from each other.

The light source part may irradiate the light at an inclined incident angle of 54 to 60 degrees in the case in which the transparent substrate is made of glass.

The upper surface foreign material detecting device of an ultra-thin transparent substrate may further include a first irradiation surface on which the light is irradiated to the upper surface of the transparent substrate and a second irradiation surface on which the light reflected through the first irradiation surface is irradiated to the lower surface of the transparent substrate, wherein in the case in which an overlapped portion is present between the first and second irradiation surfaces in a direction perpendicular to the transparent substrate, the first detecting part detects scattered light of the first irradiation surface except for the overlapped portion and the second detecting part detects scattered light of the second irradiation surface except for the overlapped portion.

[Detailed Description of Main Elements]

| | |
|---|---|
| 100: detecting device | |
| 110: light source part | 111: optical lens |
| 112: mirror | |
| 120: first detecting part | |
| 130: second detecting part | |
| G: transparent substrate | |
| P1: upper surface foreign material | P2: lower surface foreign material |

DETAILED DESCRIPTION OF EMBODIMENTS

Figure 3:
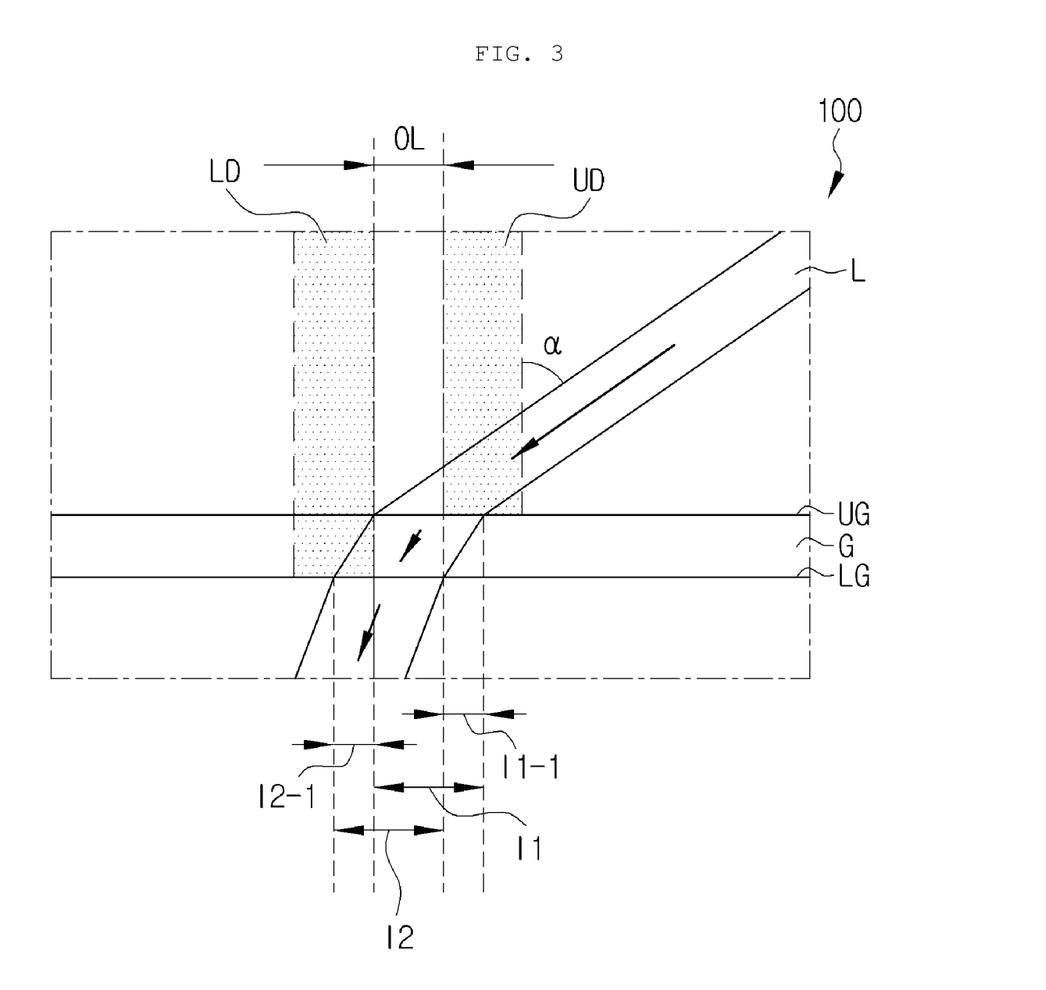
FIG. 3 is a conceptual diagram of a detecting device according to an exemplary embodiment of the present invention.

In FIG. 3, a conceptual diagram of an upper surface foreign material detecting device 100 of an ultra-thin transparent substrate according to an exemplary embodiment of the present invention (hereinafter, referred to as a "detecting device") is illustrated.

An upper surface foreign material detecting method of an ultra-thin transparent substrate G according to an exemplary embodiment of the present invention will be described with reference to FIG. 3. The detecting device 100 according to an exemplary embodiment of the present invention is configured so that light L is irradiated at an inclined angle so as to be irradiated to both of an upper surface UG and a lower surface LG of the transparent substrate G and light refracted through the upper surface UG is not reflected on the lower surface LG, but is completely refracted and transmitted through the lower surface LG.

Therefore, an upper surface foreign material and a lower surface foreign material of the transparent substrate G are distinguished from each other through an upper surface detecting device UD inspecting scattered light of a first irradiation surface I1 irradiated to the upper surface UG of the transparent substrate G and a lower surface detecting device LD inspecting scattered light of a second irradiation surface I2 passing through the first irradiation surface I1 of the transparent substrate G, refracted, and then refracted and transmitted through the lower surface LG.

That is, although an overlapped portion OL is present between the first irradiation surface I1 and the second irradiation surface I2 because the transparent substrate is the ultra-thin transparent substrate G, since a third irradiation surface I3 (See Background) on which light reflected on the lower surface LG is irradiated to the upper surface of the transparent substrate G is removed, an upper surface detecting device UD is disposed on the first irradiation surface I1-1 except for the overlapped portion OL, and a lower surface detecting device LD is disposed on the second irradiation surface I2-1 except for the overlapped portion OL to distinguish the upper surface foreign material and the lower surface foreign material of the transparent substrate G from each other.

Here, in the present invention, the following characteristics are used in order to remove the light reflected on the lower surface LG.

Figure 4:
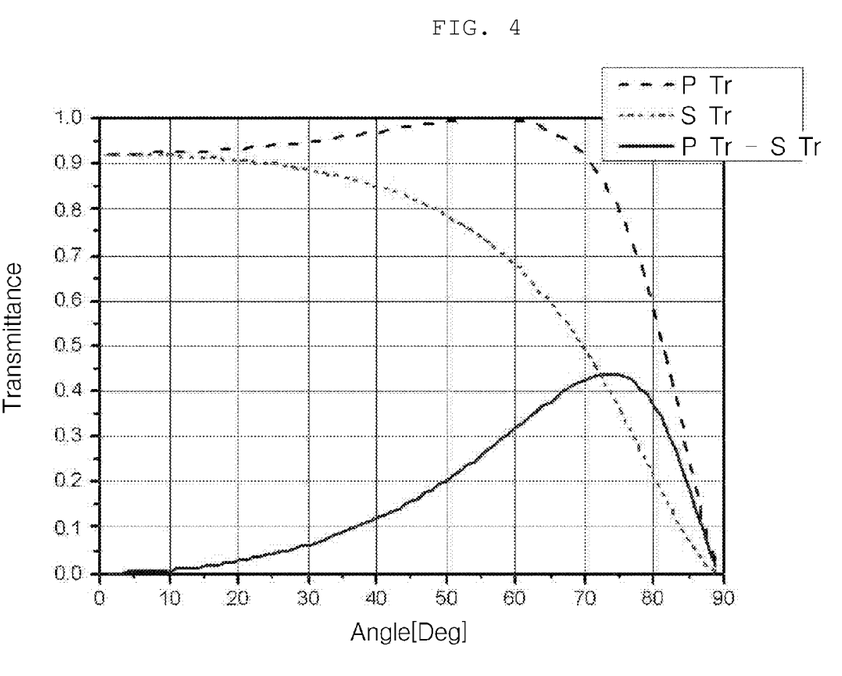
FIG. 4 is a graph illustrating transmittances of P-polarized light and S-polarized light depending on an incident angle of light.

In FIG. 4, a graph of transmittances of P-polarized light and S-polarized light depending on an incident angle of light in the case in which the transparent substrate is made of glass is illustrated (a horizontal axis indicates an incident angle of light, a vertical axis indicates a transmittance, a red color indicates P-polarized light, and a blue color indicates S-polarized light). As illustrated in FIG. 4, it may be appreciated that a transmittance of the P-polarized light is 1.0 when the incident angle is in the vicinity of 55 degrees. That is, it may be appreciated that when the P-polarized light is irradiated to the transparent substrate at an incident angle of 55 degrees, the light irradiated to the lower surface of the transparent substrate is completely transmitted without being reflected.

Therefore, in the detecting device 100 according to an exemplary embodiment of the present invention, the light reflected on the lower surface of the transparent substrate is removed using the P-polarized light as a light source and limiting the incident angle to 50 to 60 degrees, more preferably, 55 degrees. The above-mentioned case corresponds to the case in which the transparent substrate G is made of the glass, and in the case in which the transparent substrate G is made of transparent materials other than the glass, the above-mentioned effect may be accomplished when the light is irradiated at an incident angle corresponding to a Brewster angle of each substrate material.

Hereinafter, an exemplary embodiment of the present invention will be described in detail with reference to the accompanying drawings.

Figure 5:
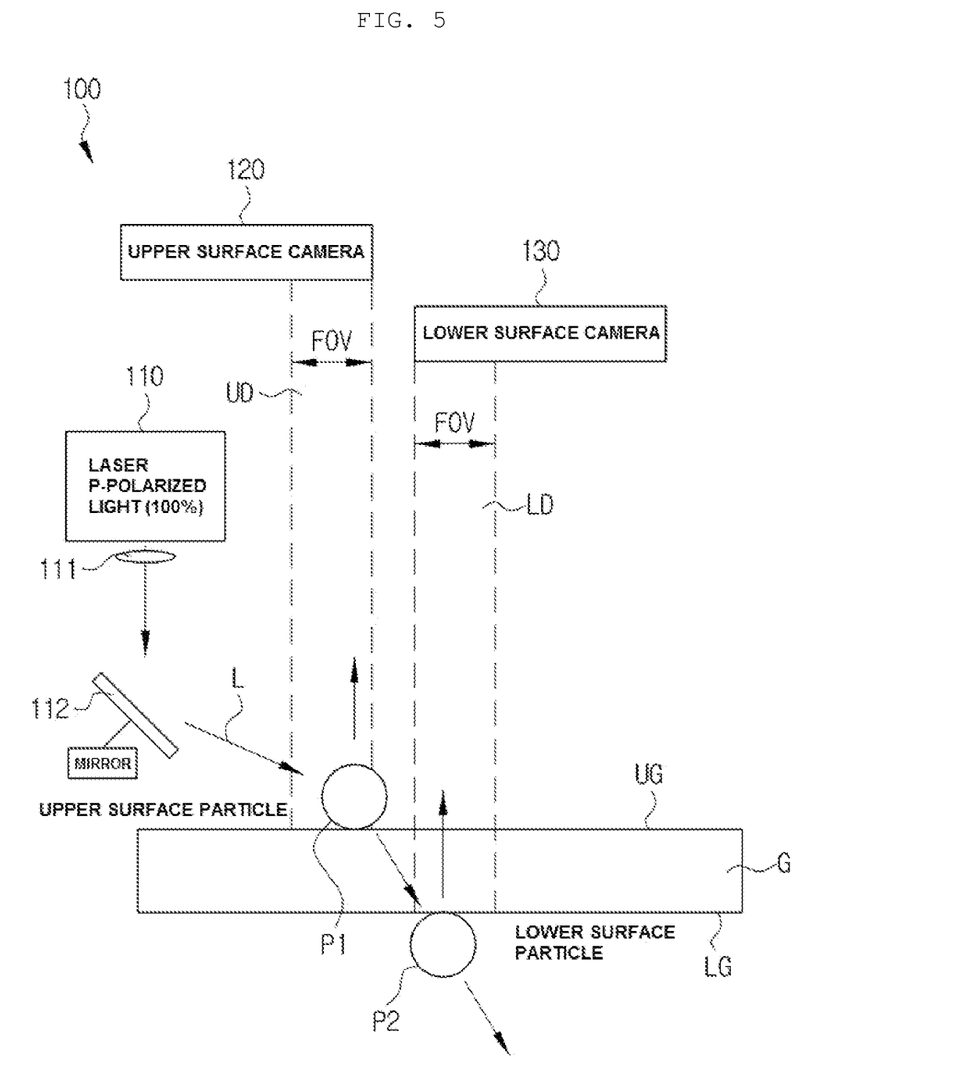
FIG. 5 is a schematic view of a detecting device according to an exemplary embodiment of the present invention.

In FIG. 5, a schematic view of the detecting device 100 according to an exemplary embodiment of the present invention is illustrated. As illustrated in FIG. 5, the detecting device 100 is configured to include a light source part 110, an optical lens 111, a mirror 112, a first detecting part 120, a second detecting part 130, and the transparent substrate G.

The light source part 110, which is a component for irradiating light to the transparent substrate G, includes a P-polarized light source irradiating P-polarized light to the transparent substrate G. The light irradiated from the light source part 110 is accumulated through the optical lens 111, and an incident angle of the light may be adjusted through the mirror 112. Here, the incident angle may be 55 degrees, as described above.

The first detecting part 120 is configured to detect scattered light of the light irradiated to the first irradiation surface I1 formed on the upper surface UG of the transparent substrate G.

The second detecting part 130 is configured to detect scattered light of the light irradiated to the second irradiation surface I2 formed on the lower surface LG of the transparent substrate G.

When the light is irradiated in a state in which a foreign material is not present on the transparent substrate G, the light passes through the transparent substrate G as it is, such that the scattered light is not generated and is not detected by the first and second detecting parts 120 and 130 having the configuration as described above, and it is decided by a controlling part deciding detection signals of the first and second detecting parts 120 and 130 that the foreign material is not present on the transparent substrate G.

On the other hand, when the light is irradiated in a state in which the foreign material is attached onto the upper surface or the lower surface of the transparent substrate G, the scattered light is generated on the foreign material by the irradiated light and is detected by the first or second detecting part 120 or 130, and it is decided by the controlling part deciding the detection signals of the first and second detecting parts 120 and 130 that the foreign material has been detected on the transparent substrate G.

Figure 6:
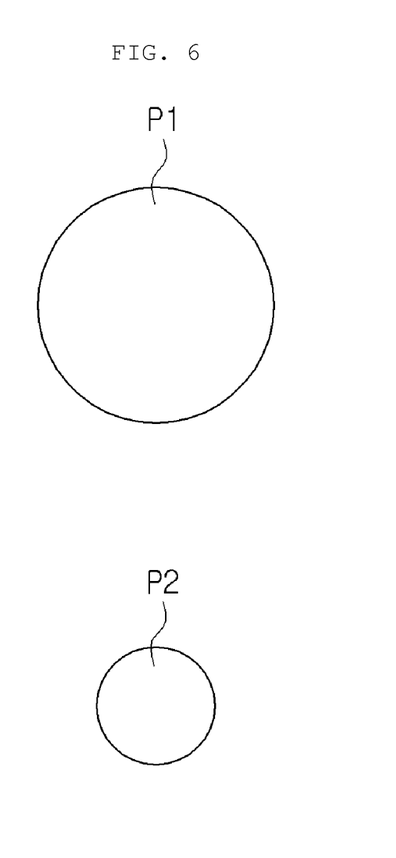
FIG. 6 is a schematic view at the time of detecting upper surface and lower surface foreign materials using the detecting device according to an exemplary embodiment of the present invention.
Figure 7:
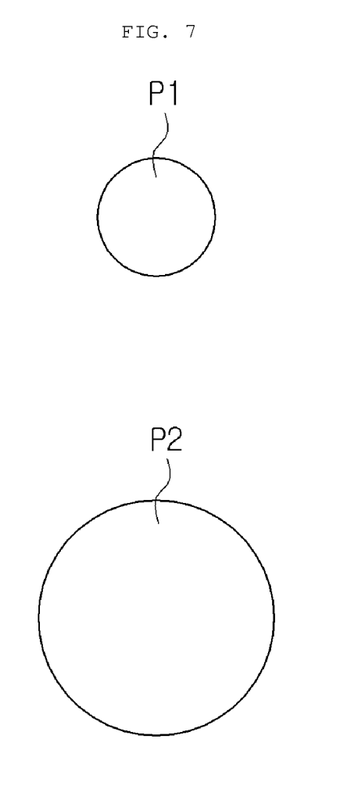
FIG. 7 is a schematic view at the time of detecting upper surface and lower surface foreign materials using the detecting device according to an exemplary embodiment of the present invention.

Here, in the case in which a first foreign material P1 is present on the upper surface UG and a second foreign material P2 is present on the lower surface LG, as illustrated in FIGS. 6 and 7, an image P1 (See FIG. 6) of the first foreign material detected through the first detecting part 120 is larger than an image P2 (See FIG. 6) of the second foreign material, and an image P1 (See FIG. 7) of the first foreign material detected through the second detecting part 130 is smaller than an image P2 (See FIG. 7) of the second foreign material, such that the upper surface foreign material and the lower surface foreign material may be distinguished from each other.

The upper surface foreign material detecting device of an ultra-thin transparent substrate according to an exemplary embodiment of the present invention having the configuration as described above may distinguish and detect the upper surface foreign material and the lower surface foreign material of the ultra-thin transparent substrate having a thickness of 0.3 T or less from each other, which may not be distinguished from each other by the existing foreign material detecting device distinguishing the upper surface foreign material and the lower surface foreign material of the transparent substrate from each other using the general upper surface detecting part and lower surface detecting part.

The present invention is not to be construed as being limited to the above-mentioned exemplary embodiment. The present invention may be applied to various fields and may be variously modified by those skilled in the art without departing from the scope of the present invention claimed in the claims. Therefore, it is obvious to those skilled in the art that these alterations and modifications fall in the scope of the present invention.

What is claimed is:

1. An upper surface foreign material detecting device of an ultra-thin transparent substrate, comprising:
   a light source part irradiating light to a transparent substrate and irradiating light so as to be inclined at a Brewster angle corresponding to a material of the transparent substrate;
   a first detecting part detecting scattered light of a foreign material attached to an upper surface of the transparent substrate by the irradiated light;
   a second detecting part detecting scattered light of a foreign material attached to a lower surface of the transparent substrate by the irradiated light; and
   a control part determining that the foreign material which detected through the first detecting part and the second detecting part is a foreign material attached to the upper surface of the transparent substrate when a size of the foreign material detected through the first detecting part is larger than a size of the foreign material detected through the second detecting part, and determining that the foreign material is a foreign material attached to the lower surface of the transparent substrate when a size of the foreign material detected through the first detecting part is smaller than a size of the foreign material detected through the second detecting part.

2. The upper surface foreign material detecting device of an ultra-thin transparent substrate of claim 1, wherein the light source part irradiates the light at an inclined incident angle of 54 to 60 degrees in the case in which the transparent substrate is made of glass.

3. The upper surface foreign material detecting device of an ultra-thin transparent substrate of claim 1, further comprising a first irradiation portion of the upper surface on which the light is irradiated to the upper surface of the transparent substrate and a second irradiation portion of the lower surface on which the light reflected through the first irradiation surface is irradiated to the lower surface of the transparent substrate, wherein in the case in which an overlapped portion is present between the first and second irradiation surfaces in a direction perpendicular to the transparent substrate, the first detecting part detects scattered light of the first irradiation surface except for the overlapped portion and the second detecting part detects scattered light of the second irradiation surface except for the overlapped portion.

4. An upper surface foreign material detecting device of an ultra-thin transparent substrate, comprising:

a light source part irradiating light to a transparent substrate and irradiating light so as to be inclined at a Brewster angle corresponding to a material of the transparent substrate;

a first detecting part detecting scattered light of a foreign material attached to an upper surface of the transparent substrate by the irradiated light;

a second detecting part detecting scattered light of a foreign material attached to a lower surface of the transparent substrate by the irradiated light;

a control part comparing brightness of the scattered light detected through the first detecting part and brightness of the scattered light detected through the second detecting part to distinguish the foreign material attached to the upper surface of the transparent substrate and the foreign material attached to the lower surface of the transparent substrate from each other; and a first irradiation portion of the upper surface on which the light is irradiated to the upper surface of the transparent substrate and a second irradiation portion of the lower surface on which the light reflected through the first irradiation surface is irradiated to the lower surface of the transparent substrate, wherein in the case in which an overlapped portion is present between the first and second irradiation surfaces in a direction perpendicular to the transparent substrate, the first detecting part detects scattered light of the first irradiation surface except for the overlapped portion and the second detecting part detects scattered light of the second irradiation surface except for the overlapped portion.

* * * * *